(12) United States Patent
Goto et al.

(10) Patent No.: US 9,068,825 B2
(45) Date of Patent: Jun. 30, 2015

(54) OPTICAL MEASUREMENT DEVICE AND OPTICAL MEASUREMENT METHOD

(71) Applicant: SEIKO EPSON CORPORATION, Tokyo (JP)

(72) Inventors: Kenji Goto, Nagano (JP); Hideaki Yamada, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/461,667

(22) Filed: Aug. 18, 2014

(65) Prior Publication Data

US 2015/0006107 A1 Jan. 1, 2015

Related U.S. Application Data

(63) Continuation of application No. 13/749,224, filed on Jan. 24, 2013, now Pat. No. 8,842,277.

(30) Foreign Application Priority Data

Jan. 30, 2012 (JP) ................. 2012-016737

(51) Int. Cl.
*G01J 4/00* (2006.01)
*G01B 11/26* (2006.01)
*G01N 21/21* (2006.01)
*G01N 33/02* (2006.01)
*G01N 33/14* (2006.01)

(52) U.S. Cl.
CPC . *G01B 11/26* (2013.01); *G01J 4/00* (2013.01); *G01N 21/21* (2013.01); *G01N 33/025* (2013.01); *G01N 33/143* (2013.01)

(58) Field of Classification Search
USPC ........... 356/364–370, 244, 246; 250/216, 225
See application file for complete search history.

(56) References Cited

U.S. PATENT DOCUMENTS 5,168,326 A 12/1992 Tokieda et al.

FOREIGN PATENT DOCUMENTS

WO 99/30132 A1 6/1999

*Primary Examiner* — Tri T Ton
(74) *Attorney, Agent, or Firm* — Global IP Counselors, LLP

(57) ABSTRACT

In a first optical measurement device, light which is output from a light source is subject to linear polarizing in a polarizing unit, and is input to a test object A. Transmitted light which has passed through the test object A is orthogonally separated in an orthogonal separation unit, and the light which is orthogonally separated in the orthogonal separation. unit is received in two light receiving units. In addition, amount of light of the transmitted light is determined by a control unit, and a difference between received light levels which are received in the light receiving unit is normalized using the amount of light which is determined in a transmitted amount of light determination unit, and then the angle of optical rotation is calculated by the angle of optical rotation calculation unit.

3 Claims, 5 Drawing Sheets

620

| | SWITCHING SETTING OF SWITCH | AMPLIFICATION FACTOR |
|---|---|---|
| SUBTRACTION | S1 | G1 |
| ADDITION | S2 | G2 |

OPTICAL MEASUREMENT DEVICE AND OPTICAL MEASUREMENT METHOD

CROSS-REFERENCE TO RELATED APPLICATIONS

This is a continuation application of U.S. patent application Ser. No. 13/749,224 filed on Jan. 24, 2013. This application claims priority to Japanese Patent Application No. 2012-016737 filed on Jan. 30, 2012. The entire disclosures of U.S. patent application Ser. No. 13/749,224 and Japanese Patent Application No. 2012-016737 are hereby incorporated herein by reference.

BACKGROUND

1. Technical Field

The present invention relates to an optical measurement device, or the like, for measuring an optical rotation angle.

2. Related Art

It is possible to know the composition of a material without making direct contact by measuring light which has passed through the material. For example, it is possible to estimate concentration of a material by measuring an angle of optical rotation. Optical rotation refers to a property in which, when linearly polarized light passes through an optically active substance such as glucose, for example, a plane of polarization thereof rotates.

As a technology using the property of optical rotation, a technology is disclosed in WO 99/30132, for example, in which linearly polarized light which has passed through a test object is orthogonally separated, polarized components thereof are received by two respective light receiving elements, and an angle of optical rotation is measured from a difference between output levels of both the light receiving elements.

In the technology of measuring an angle of optical rotation which is disclosed in WO 99/30132, the angle of optical rotation is measured from a difference between output levels of the two light receiving elements. However, there is a problem in this measuring method. As light which is radiated to the test object, laser light is generally used, however, there is a case in which an output fluctuation, which is referred to as a so-called return light noise, occurs in a laser device such as a semiconductor laser which outputs laser light. It is a phenomenon in which oscillation of a laser becomes unstable since a part of light which is output from the laser device returns to the laser device again by being reflected. In this case, a so-called fluctuation in amount of light occurs in which amount of light of transmitted light which has passed through the test object fluctuates.

In addition, when a test object having a plurality of components whose absorbance is different from each other is measured, each component is not necessarily distributed equally in the test object. That is, the fluctuation in amount of light of transmitted light which passes through the test object easily occurs, since the absorbance becomes different depending on a mixed state of each component, a radiated position of the laser, the passage of time, or the like when performing the measuring.

When such a fluctuation in amount of light occurs, it is not possible to guarantee that the angle of optical rotation, which is simply calculated from a difference between received light levels in the light receiving elements, is a correct measurement value. This is because, when the fluctuation in amount of light occurs, the received light levels in the light receiving elements are totally changed, and the difference between the received light levels is changed. For example, though it is an extreme example, when amount of light of the transmitted light is reduced to ½, a difference between received light levels is reduced to ½, since the light receiving level in the light receiving element is reduced to ½. Consequently, the method of measuring an angle of optical rotation in the related art determined from the difference in received light levels, is unable to provide the correct angle of optical rotation.

SUMMARY

An advantage of some aspects of the invention is to propose a new method in which an angle of optical rotation can be correctly measured.

An optical measurement device according to an aspect of the invention comprises an orthogonal separation unit, at least two light receiving units, and an optical rotation angle calculation unit. The orthogonal separation unit is configured to orthogonally separate transmitted light in which linearly polarized light has passed through a test object. The at least two light receiving units are configured to receive light which is orthogonally separated in the orthogonal separation unit. The optical rotation angle calculation unit includes a transmitted light amount determination unit, an amplification factor setting unit, an amplification unit, and a controller. The transmitted light amount determination unit is configured to determine amount of light of the transmitted light. The amplification factor setting unit is configured to set a first amplification factor to the amount of light of the transmitted light and set a second amplification factor to a difference between received light levels which are received in the light receiving units, and the first amplification factor and the second amplification factor are different from each other. The amplification unit is configured to amplify the amount of light of the transmitted light with the first amplification factor and the difference between the received light levels with the second amplification factor. The controller is configured to calculate an angle of optical rotation after normalizing the difference between the received light levels using the amount of light of the transmitted light.

According to the optical measurement device of the aspect, the optical rotation angle calculation unit has a subtractor obtaining the difference between the received light levels.

According to the optical measurement device of the aspect, the optical rotation angle calculation unit has an adder obtaining a sum of the received light levels which are received in the light receiving unit, and the transmitted light amount determination unit determines the amount of light using the sum of the received light levels.

BRIEF DESCRIPTION OF THE DRAWINGS

The invention will be described with reference to the accompanying drawings, wherein like numbers reference like elements.

FIG. 2 is a table showing a data structure example of parameter data for control.

DESCRIPTION OF EXEMPLARY EMBODIMENTS

Hereinafter, examples of preferable embodiments of the invention will be described with reference to drawings. However, as a matter of course, embodiments to which the invention is applicable are not limited to embodiments described herein.

1. First Embodiment 1-1. Configuration

Figure 1:
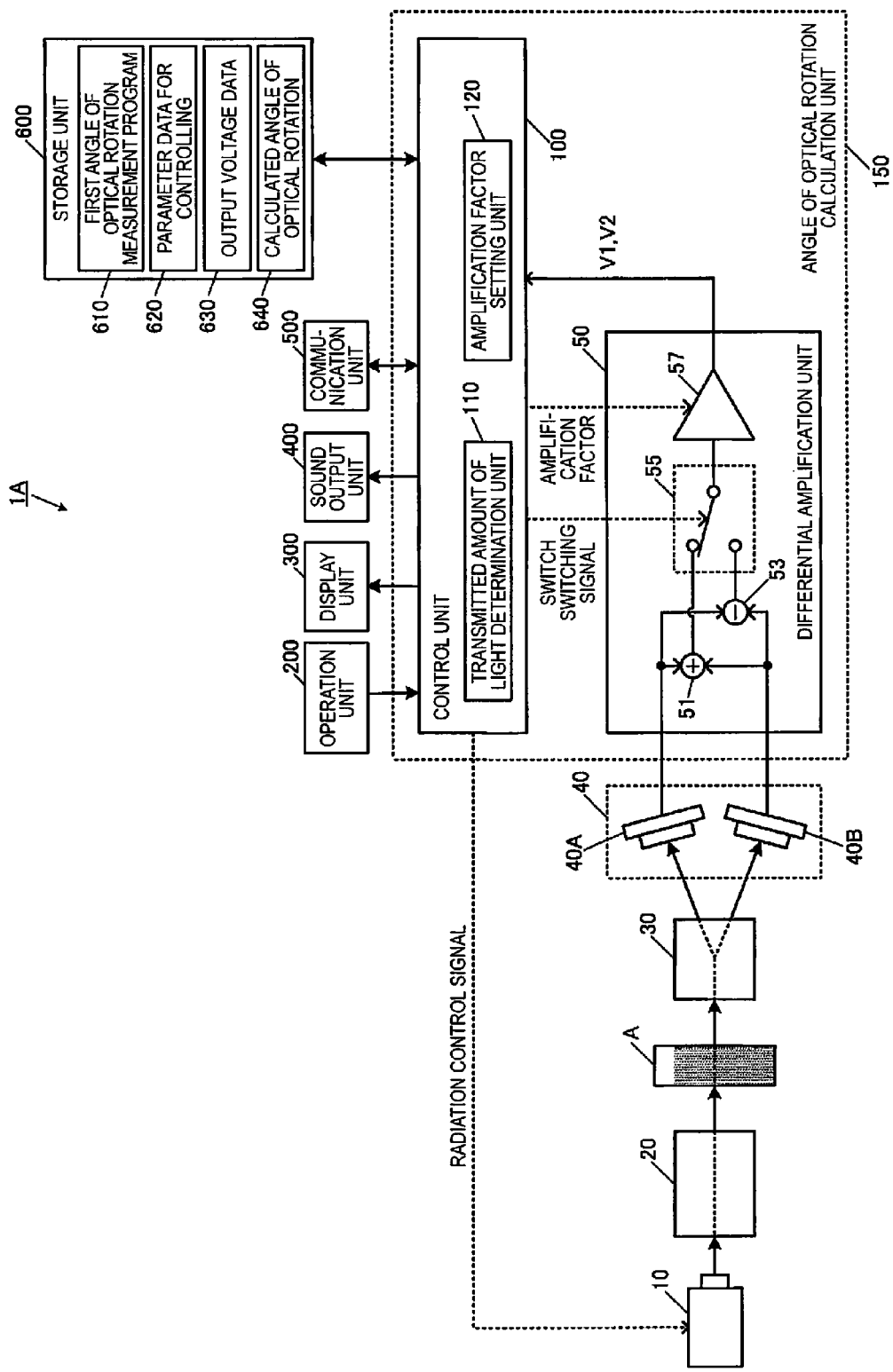
FIG. 1 is a diagram which illustrates a configuration example of a first optical measurement device.

FIG. 1 is a diagram which illustrates a configuration example of a first optical measurement device 1A according to a first embodiment. The first optical measurement device 1A is mainly configured by including a light source 10, a polarizing unit 20, an orthogonal separation unit 30, a light receiving unit 40, a differential amplification unit 50, a control unit 100, an operation unit 200, a display unit 300, a sound output unit 400, a communication unit 500, and a storage unit 600.

A test object A is arranged between the polarizing unit 20 and the orthogonal separation unit 30. It is possible to set the test object A to any sample such as a solid matter or liquid which includes an optically active substance. In the embodiment, the test object A is set to a reagent whose main component is glucose, and a property of optical rotation of the test object A is estimated by measuring the angle of optical rotation of the test object A by receiving the transmitted light which passes through the test object A.

The light source 10 is a laser device which generates and outputs light. For example, the light source is configured by including a semiconductor laser (laser diode). The light source 10 radiates laser light with a phase of a predetermined wavelength (for example, 650 nanometer [nm]) from an end face which is a half mirror.

The polarizing unit 20 is a polarizing element (polarizer) which converts output light from the light source 10 to linearly polarized light, and is configured by including, for example, a polarizing optical element such as a polarizing prism. As the polarizing unit 20, for example, it is possible to apply a Glan Thompson prism which is a Glan type polarizer.

In the orthogonal separation unit 30, the transmitted light in which the linearly polarized light passed through the test object A is separated into orthogonal components which form a predetermined angle of aperture, that is, polarized components which are different by 90° from each other. As the orthogonal separation unit 30, for example, it is possible to apply the Wollaston prism as a type of polarizing optical element.

The light receiving unit 40 is an element which receives light which is orthogonally separated by the orthogonal separation unit 30, and is configured by including a light detector such as a photo diode. The light receiving unit 40 is configured by including at least two light receiving units. For example, the light receiving unit 40 is configured by including a P polarized light receiving unit 40A and an S polarized light receiving unit 40B. In addition, the polarized components (P component and S component) which are orthogonally separated by the orthogonal separation unit 30, and are orthogonal to each other are detected, a voltage corresponding to the amount of light is output to the differential amplification unit 50 by performing a photoelectric conversion. In descriptions below, a voltage which is subject to the photoelectric conversion in the P polarized light receiving unit 40A is referred to as a "P polarization voltage", and a voltage which is subject to the photoelectric conversion in the S polarized light receiving unit 40B is referred to as an "S polarization voltage".

The differential amplification unit 50 is a calculation unit which amplifies a difference and the sum of the received light levels in the light receiving unit 40 for detection, and is configured by including an adder 51, a subtracter 53, a switch 55, and an amplification circuit 57. Outputs of the P polarized light receiving unit 40A and S polarized light receiving unit 40B are subject to an addition and subtraction in the adder 51 and the subtracter 53, respectively, and are configured such that any one of the addition result and the subtraction result is selected in the switch 55, and is amplified in the amplification circuit 57. Switching of the switch 55, and the amplification factor of the amplification circuit 57 are controlled by an instruction signal from the control unit 100.

The control unit 100 performs switching of the switch 55 in a predetermined cycle. According to the switching control by the control unit 100, the differential amplification unit 50 outputs a voltage corresponding to a difference between received light levels, and a voltage corresponding to the sum of the received light levels by calculating in a time division method. Hereinafter, descriptions will be made by referring to the voltage corresponding to the difference between received light levels as a "subtraction output voltage", and the voltage corresponding to the sum of the received light levels as an "addition output voltage".

In addition, the control unit 100 variably sets the amplification factor of the differential amplification unit 50 (amplification circuit 57). Specifically, when the switch 55 is switched to the subtracter 53 side, the subtraction output voltage is amplified with a first amplification factor "G1" by setting the amplification factor to the first amplification factor "G1". In contrast to this, when the switch 55 is switched to the adder 51 side, the addition output voltage is amplified with a second amplification factor "G2" by setting the amplification factor to the second amplification factor "G2" which is lower than the first amplification factor "G1".

The control unit 100 includes a transmitted amount of light determination unit 110 which determines amount of light of transmitted light from the addition output voltage (sum of received light levels) which is output from the differential amplification unit 50, and an amplification factor setting unit 120 which variably sets an amplification factor of the differential amplification unit 50. An angle of optical rotation calculation unit 150 which calculates the angle of optical rotation is configured by the differential amplification unit 50 and the control unit 100 in the first optical measurement device 1A.

The control unit 100 is a control unit which collectively controls each unit of the first optical measurement device 1A, and is configured by including a microprocessor such as a CPU (Central Processing Unit), or a DSP (Digital Signal Processor), an ASIC (Application Specific Integrated Circuit), or the like.

The operation unit 200 is an input unit which is configured by including a button switch, or the like, and outputs a signal of a pressed button to the control unit 100. Due to an operation of the operation unit 200, various instruction inputs such as an instruction on starting the measurement of the angle of optical rotation, and the like, are performed.

The display unit 300 is configured by including an LCD (Liquid Crystal Display), or the like, and is a display unit which performs various displays based on a display signal which is input from the control unit 100. Information on the measured angle of optical rotation, or the like is displayed on the display unit 300.

The sound output unit 400 is a sound output unit which outputs various sounds based on a sound output signal which is input from the control unit 100.

The communication unit 500 is a communication unit which transmits and receives information which is used in the unit to and from an external information processing device according to a control of the control unit 100. As a communication method of the communication unit 500, various methods such as a type in which a wired connection is made through a cable which is conformed with a predetermined communication standard, a type in which a connection is made through an intermediate device which is used also as a battery charger which is referred to as a cradle, or a type in which a wireless connection is made using a near field wireless communication are applied.

The storage unit 600 is configured by including a storage unit such as a ROM (Read Only Memory), a flash ROM, or a RAM (Random Access Memory). The storage unit 600 stores a system program of the first optical measurement device 1A, various programs for executing various functions such as a measuring function of the angle of optical rotation, data, or the like. In addition, a work area in which data in the middle of processing of various processes, a processing result, or the like is temporarily stored is included.

Figure 3:
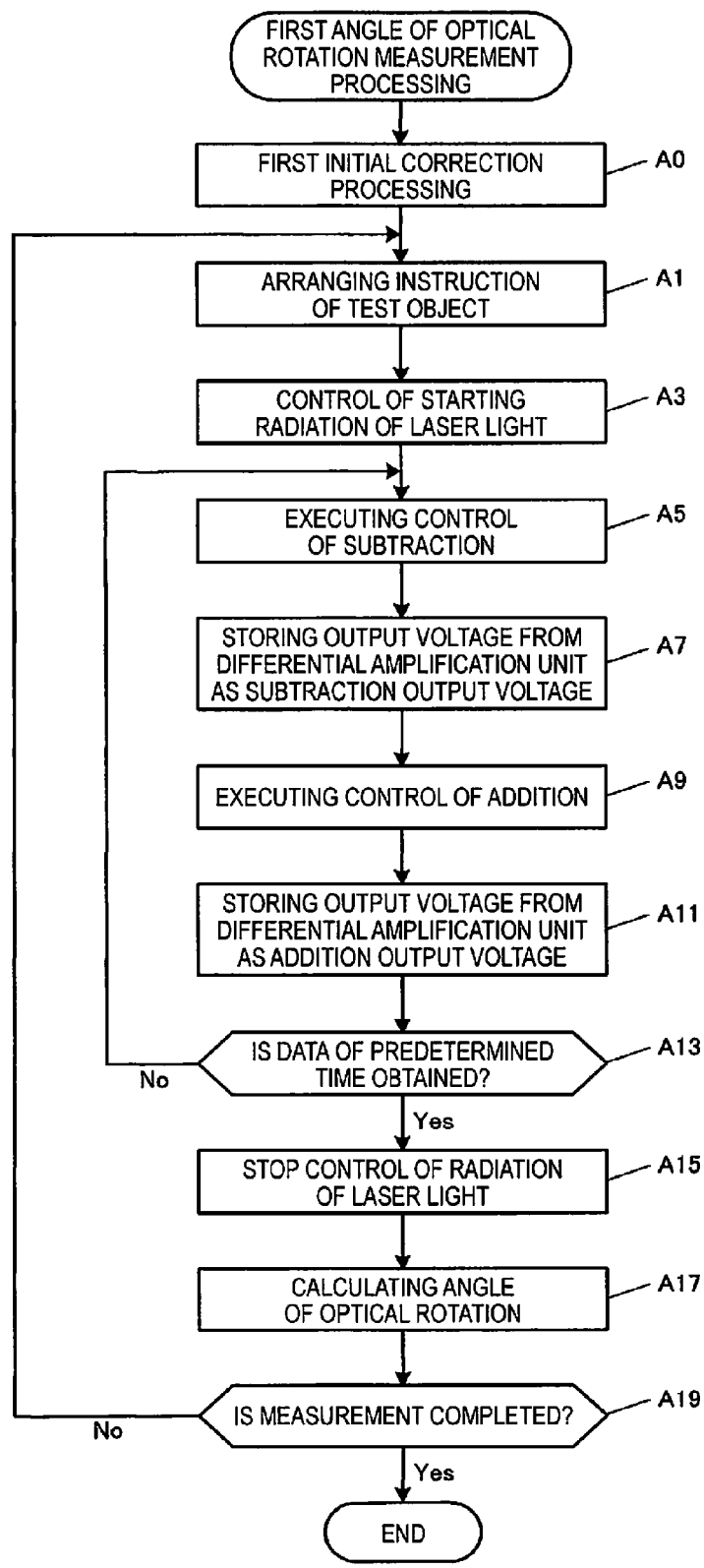
FIG. 3 is a flowchart which illustrates a flow of a first angle of optical rotation measurement processing.

The storage unit 600 is stored with a first angle of optical rotation measurement program 610 which is read out by the control unit 100, and is executed as first angle of optical rotation measurement processing (refer to FIG. 3). The first angle of optical rotation measurement processing will be described in detail later using a flowchart.

In addition, the storage unit 600 is stored with parameter data for control 620, output voltage data 630, and a calculated angle of optical rotation 640.

FIG. 2 is a table showing a data structure example of a parameter data for control 620.

The parameter data for control 620 is data which is used when the control unit 100 controls the differential amplification unit 50, and is prescribed in the form of a table in which switching setting of the switch 55, and the amplification factor of the amplification circuit 57 are correlated with each other regarding the respective subtraction and addition. The control unit 100 controls the differential amplification unit 50 according to the parameter data for control 620.

The output voltage data 630 is data in which a voltage which is output from the differential amplification unit 50 is stored. Specifically, the output voltage data 630 is stored with the subtraction output voltage and the addition output voltage in time sequence which are alternately output from the differential amplification unit 50 in the time division method so that it is possible to identify what output voltage it is.

In addition, the calculated angle of optical rotation 640 is data in which an angle of optical rotation which is calculated by the control unit 100 is stored.

1-2. Calculation Method of Angle of Optical Rotation

A calculation method of the angle of optical rotation according to the first embodiment will be described in detail.

The amount of light of the transmitted light which transmitted the test object A is set to "$Ea^2$", an incident angle of linearly polarized light with respect to the orthogonal separation unit 30 is set to "$\theta_0$", and the angle of optical rotation by the test object A is set to "$\theta$". At this time, electric field components of P polarization and S polarization are expressed by "$Ea \cos(\theta+\theta_0)$", and "$Ea \sin(\theta+\theta_0)$", respectively.

Accordingly, the P polarization voltage and the S polarization voltage are expressed by "$Ea^2 \cos^2(\theta+\theta_0)$", and "$Ea^2 \sin^2(\theta+\theta_0)$", respectively.

At this time, it is possible to obtain a subtraction voltage "Vs" as in the following expression (1) by subtracting the S polarization voltage from the P polarization voltage. In addition, it is possible to obtain an addition voltage "Va" as in the following expression (2) by adding the P polarization voltage to the S polarization voltage.

$$Vs = Ea^2\cos^2(\theta+\theta_0) - Ea^2\sin^2(\theta+\theta_0) \quad (1)$$
$$= Ea^2(\cos^2(\theta+\theta_0) - \sin^2(\theta+\theta_0))$$

$$Va = Ea^2\cos^2(\theta+\theta_0) + Ea^2\sin^2(\theta+\theta_0) \quad (2)$$
$$= Ea^2(\cos^2(\theta+\theta_0) + \sin^2(\theta+\theta_0))$$
$$= Ea^2$$

The differential amplification unit 50 calculates the subtraction voltage "Vs" and the addition voltage "Va" which are expressed in the expressions (1) and (2), and amplifies the calculation result using an amplification factor which is instructed from the control unit 100. Since an amplification factor with respect to the subtraction voltage "Vs" is "G1", and an amplification factor with respect to the addition voltage "Va" is "G2", the subtraction output voltage "V1" and the addition output voltage "V2" which are output from the differential amplification unit 50 become the following expressions (3), and (4), respectively.

$$V1 = G1 \cdot Vs \quad (3)$$
$$= G1 \cdot Ea^2(\cos^2(\theta+\theta_0) - \sin^2(\theta+\theta_0))$$

$$V2 = G2 \cdot Va \quad (4)$$
$$= G2 \cdot Ea^2$$

It is possible to derive the following expression (5) from the expressions (3) and (4).

$$\frac{G2}{G1}\frac{V1}{V2} = \cos^2(\theta+\theta_0) - \sin^2(\theta+\theta_0) \quad (5)$$
$$= \cos 2(\theta+\theta_0)$$

Accordingly, it is possible to calculate the angle of optical rotation "$\theta$" from the expression (5) as in the following expression (6).

$$\theta = \frac{1}{2}\arccos\left(\frac{G2}{G1}\frac{V1}{V2}\right) - \theta_0 \quad (6)$$
$$= \frac{1}{2}\arccos\left(C1\frac{V1}{V2}\right) - \theta_0$$

However, it is replaced with "G2/G1=C1".

According to the expression (6), two parameter values of "C1" and "$\theta_0$" are necessary in order to calculate the angle of optical rotation "$\theta$". For example, the "C1" can be obtained from a ratio of the first amplification factor "G1" to the second amplification factor "G2" which is prescribed in the parameter data for control 620, and the "$\theta_0$" can be mechanically set to a predetermined angle, or the like.

Since an angle of optical rotation which is expressed at an extremely minute angle is set to a measurement target, the above described parameter value greatly influences on measurement precision of the angle of optical rotation. An error which is caused by a temperature property of a circuit element, precision in a design value, or the like, can be included in the amplification factor in design (design value) of the differential amplification unit 50. It is also considered that the measurement precision of the angle of optical rotation deteriorates due to the error.

Therefore, according to the embodiment, it is possible to set the "C1" and "$\theta_0$" by performing an initial correction. Specifically, an equation which derives an angle of optical rotation is set up using two or more kinds of substances whose angles of optical rotation are well-known as the test object A. Since there are two unknown number of "C1" and "$\theta_0$", two unknown numbers are obtained when two or more equations are set up. A solution of the equation can be calculated using, for example, a well-known numerical calculation such as a least squares method.

1-3. Flow of Processing

FIG. 3 is a flowchart which illustrates a flow of the first angle of optical rotation measurement processing which is executed by the control unit 100 according to the first angle of optical rotation measurement program 610 which is stored in the storage unit 600.

Firstly, the control unit 100 performs a first initial correction processing (step A0). Specifically, two parameter values of "C1" and "$\theta_0$" in the expression (6) are corrected based on the above described method, or the like.

Subsequently, the control unit 100 performs an arrangement instruction of the test object A (step A1). For example, a message is displayed on the display unit 300, or a sound guidance is output from the sound output unit 400. In addition, the control unit 100 causes the light source 10 to start radiating of laser light (step A3).

Subsequently, the control unit 100 executes a control for subtraction (step A5). Specifically, a switch switching signal S1 which switches to the subtracter 53 side is output to the switch 55 by referring to the parameter data for control 620. In addition, a control signal for setting the amplification factor of the amplification circuit 57 to G1 is output to the amplification circuit 57. In addition, the control unit 100 causes the output voltage from the differential amplification unit 50 to be stored in the output voltage data 630 as the subtraction output voltage (step A7).

Subsequently, the control unit 100 executes a control for adding (step A9). Specifically, a switch switching signal S2 which switches to the adder 51 side is output to the switch 55 by referring to the parameter data for control 620. In addition, a control signal for setting the amplification factor of the amplification circuit 57 to G2 is output to the amplification circuit 57. In addition, the control unit 100 causes the output voltage from the differential amplification unit 50 to be stored in the output voltage data 630 as the addition output voltage (step A11).

Processes of the above described steps A5 to A11 are executed until data of output voltages of a predetermined time is obtained (step A13). When the data of output voltage of the predetermined time is obtained (Yes in step A13), the control unit 100 stops the radiation of laser light of the light source 10 (step A15).

Thereafter, the control unit 100 calculates the angle of optical rotation according to the expression (6) using a parameter value which is corrected in the first initial correction processing, a mean value of the subtraction output voltage, and a mean value of the addition output voltage of the predetermined time which is stored in the output voltage data 630, and stores the angle of optical rotation in the storage unit 600 as the calculated angle of optical rotation 640 (step A17).

In addition, it is also preferable to calculate the angle of optical rotation "$\theta$" using instantaneous values of the subtraction output voltage "V1" and the addition output voltage "V2", however, in order to improve calculation precision of the angle of optical rotation "$\theta$", it is effective when the angle of optical rotation "$\theta$" is calculated according to the expression (6) using, for example, a mean value of the subtraction output voltage "V1", and the addition output voltage "V2" of the predetermined time.

As is understood from the expression (6), according to the embodiment, the subtraction output voltage "V1" is divided by the addition output voltage "V2", and the angle of optical rotation "$\theta$" is calculated using the result. The addition output voltage "V2" is a voltage corresponding to amount of light of transmitted light. In addition, the subtraction output voltage "V1" is a voltage corresponding to a difference between the received light levels. Accordingly, dividing the subtraction output voltage "V1" by the addition output voltage "V2" means normalizing the difference between received light levels using the amount of light of the transmitted light, and the angle of optical rotation "$\theta$" is calculated from the difference between the normalized received light levels.

Returning to the descriptions in the flowchart in FIG. 3, when the control unit 100 determines whether or not to end the measurement of the angle of optical rotation (step A19), and determines to continue the measurement (No in step A19), after calculating the angle of optical rotation, the process returns to step A1. In addition, when it is determined to end the measurement (Yes in step A19), the first angle of optical rotation measurement processing is ended.

1-4. Effects of Operation

In the first optical measurement device 1A, light which is output from the light source 10 becomes the linearly polarized light in the polarizing unit 20, and is input to the test object A. The transmitted light which transmitted the test object A is orthogonally separated in the orthogonal separation unit 30, and the light which is orthogonally separated in the orthogonal separation unit 30 is received in at least two light receiving units 40 (40A and 40B). In addition, the amount of light of the transmitted light is determined in the control unit 100, the difference between the received light levels which are received in the light receiving unit 40 is normalized using the amount of light which is determined in a transmitted amount of light determination unit, and then the angle of optical rotation is calculated by the angle of optical rotation calculation unit 150.

If the angle of optical rotation is calculated simply using the difference between the received light levels which are received in the light receiving unit 40, when a fluctuation in the amount of light of the transmitted light occurs, it is difficult to obtain an accurate angle of optical rotation due to the fluctuation in the amount of light. However, since the amount of light of the transmitted light is determined, and the angle of optical rotation is calculated after normalizing the difference between the received light levels using the amount of light in the first optical measurement device 1A, it is possible to accurately calculate the angle of optical rotation even when the amount of light of the transmitted light fluctuates.

More specifically, the difference and the sum of the received light levels in the light receiving unit 40 are obtained in a time division method in the differential amplification unit 50. The transmitted amount of light determination unit of the control unit 100 determines the amount of light of the transmitted light using the sum of the received light levels which are received in the light receiving unit 40, and normalizes the difference between the received light levels using the determined amount of light of the transmitted light. With this configuration, it is possible to determine the amount of light of the transmitted light using a simple method such as obtaining the sum of the received light levels.

In addition, the control unit 100 variably sets the amplification factor of the differential amplification unit 50. Specifically, when the differential amplification unit 50 calculates the difference between the received light levels, the amplification factor is set to a first amplification factor, and when the differential amplification unit 50 calculates the sum of the received light levels, the amplification factor is set to a second amplification factor which is lower than the first amplification factor. Since the difference between the received light levels is a minute value, it is possible to calculate the angle of optical rotation with high precision according to the received light levels by improving resolution by setting the amplification factor high compared to a case of obtaining the sum of the received light levels.

2. Second Embodiment 2-1. Configuration

Figure 4:
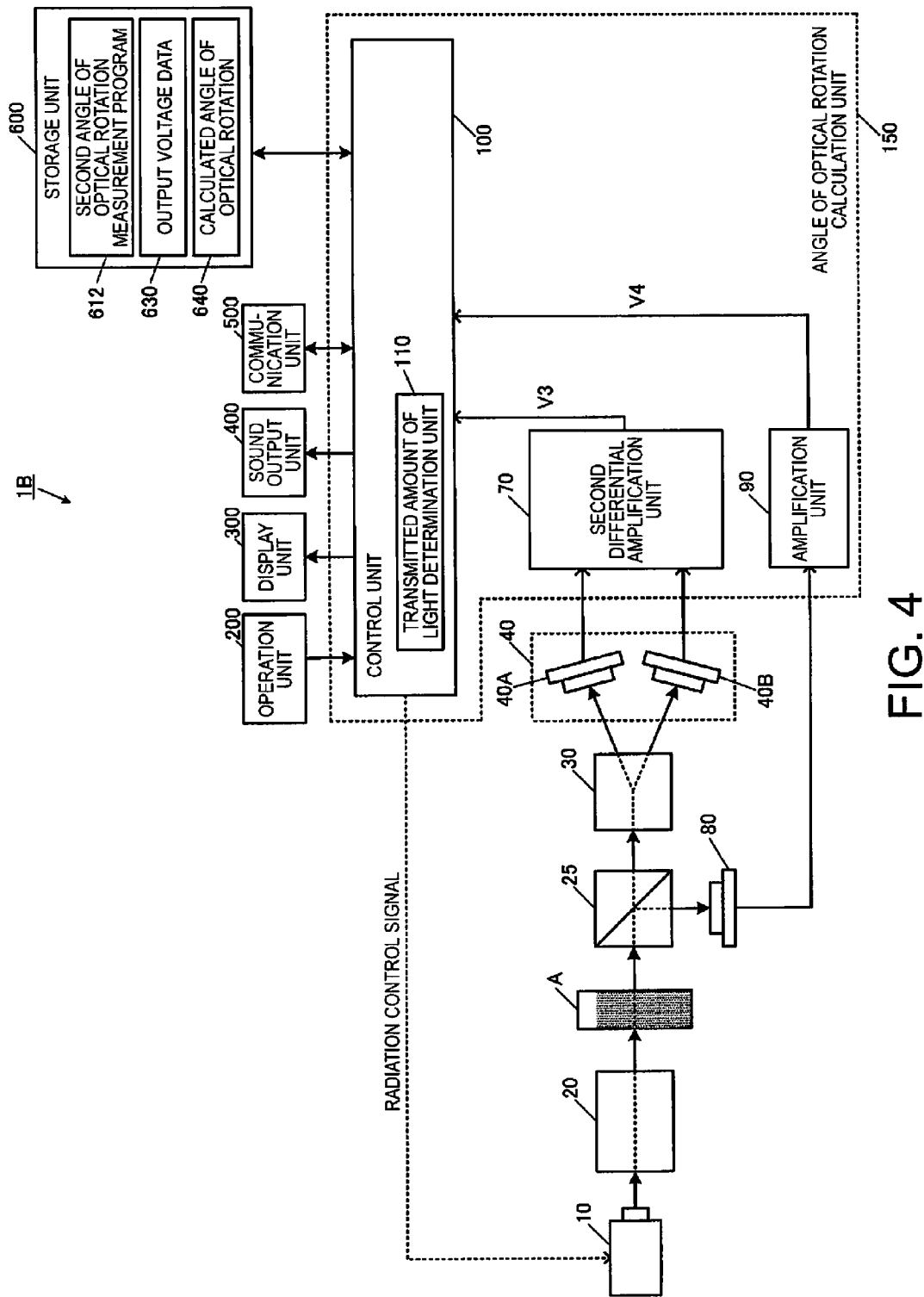
FIG. 4 is a diagram which illustrates a configuration example of a second optical measurement device.

FIG. 4 is a diagram which illustrates a configuration example of a second optical measurement device 1B in a second embodiment. The second optical measurement device 1B is configured by including a light source 10, a polarizing unit 20, a non-polarizing separation unit 25, an orthogonal separation unit 30, a light receiving unit 40, a second differential amplification unit 70, a second light receiving unit 80, an amplification unit 90, a control unit 100, an operation unit 200, a display unit 300, a sound output unit 400, a communication unit 500, and a storage unit 600. In addition, the same constituent elements as those in the first optical measurement device 1A will be given the same reference numerals, and repeated descriptions will be omitted.

In the second optical measurement device 1B, the non-polarizing separation unit 25 is provided between a test object A and the orthogonal separation unit 30. The non-polarizing separation unit 25 is a polarizing element which separates incident light into transmitted light and reflected light in a predetermined amount of light ratio while maintaining a polarized state of the incident light. It is possible to apply, for example, a non-polarizing beam splitter as the non-polarizing separation unit 25.

Light on one side which is separated by the non-polarizing separation unit 25 inputs to the orthogonal separation unit 30, and is separated into a P polarized component and S polarized component. In contrast to this, light on the other side which is separated by the non-polarizing separation unit 25 is received in the second light receiving unit 80. The light which is received in the second light receiving unit 80 is subject to photoelectric conversion, and a voltage corresponding to amount of light is output to the amplification unit 90. In addition, the light is amplified in a predetermined amplification factor in the amplification unit 90, and then is output to the control unit 100. The transmitted amount of light determination unit 110 determines amount of light of transmitted light based on received light levels of the second light receiving unit 80.

Since the amount of light separation proportion of the incident light by the non-polarizing separation unit 25 is well-known, the transmitted amount of light determination unit 110 is able to calculate the whole amount of light of the transmitted light using the light receiving level of the second light receiving unit 80, and also to calculate the amount of light which is input to the orthogonal separation unit 30.

On the other hand, the P polarization voltage which is subject to the photoelectric conversion in the P polarized light receiving unit 40A of the light receiving unit 40, and the S polarization voltage which is subject to the photoelectric conversion in the S polarized light receiving unit 40B are output to the second differential amplification unit 70. In the second differential amplification unit 70, a difference between the P polarization voltage and the S polarization voltage is calculated, and is output to the control unit 100 after being amplified with a predetermined amplification factor. Accordingly, only the subtraction output voltage which is mentioned in the first embodiment is output from the second differential amplification unit 70.

In addition, the storage unit 600 is stored with a second angle of optical rotation measurement program 612 which is executed as second angle of optical rotation measurement processing (refer to FIG. 5) by the control unit 100, output voltage data 630, and a calculated angle of optical rotation 640.

2-2. Calculation Method of Angle of Optical Rotation

A calculation method of the angle of optical rotation according to the second embodiment will be described in detail.

Transmitted light which has transmitted the test object A is subject to a non-polarizing separation into "T1:T2" by the non-polarizing separation unit 25 (here, T1+T2=1). Specifically, amount of light "$Ea^2$" of the transmitted light is separated into "T1:T2", light of amount of light "$T1 \cdot Ea^2$" is received in the light receiving unit 40, and light of amount of light "$T2 \cdot Ea^2$" is received in the second light receiving unit 80.

At this time, the P polarizing voltage and the S polarizing voltage which are received in the P polarized light receiving unit 40A and the S polarized light receiving unit 40B, and are subject to the photoelectric conversion are expressed by "$T1 \cdot Ea^2 \cos^2(\theta+\theta_0)$" and "$T1 \cdot Ea^2 \sin^2(\theta+\theta_0)$", respectively. Accordingly, the subtraction voltage "Vs" when the S polarizing voltage is subtracted from the P polarizing voltage is expressed in the following expression (7).

$$Vs = T1 \cdot Ea^2 (\cos^2(\theta+\theta_0) - \sin^2(\theta+\theta_0)) \quad (7)$$

On the other hand, a voltage "V" which is received in the second light receiving unit 80, and is subject to the photoelectric conversion is given in the following expression (8).

$$V = T2 \cdot Ea^2 \quad (8)$$

The second differential amplification unit 70 amplifies the subtraction voltage "Vs" which is expressed in the expression (7) with an amplification factor "G3". As a result, a subtraction output voltage "V3" which is output from the second differential amplification unit 70 is expressed as in the following expression (9).

$$V3 = G3 \cdot Vs \quad (9)$$
$$= G3 \cdot T1 \cdot Ea^2 (\cos^2(\theta+\theta_0) - \sin^2(\theta+\theta_0))$$

In addition, the amplification unit 90 amplifies the voltage "V" which is expressed in the expression (8) with an amplification factor "G4". As a result, an output voltage "V4" which is output from the amplification unit 90 is expressed as in the following expression (10).

$$V4 = G4 \cdot V \quad (10)$$
$$= G4 \cdot T2 \cdot Ea^2$$

The following expression (11) is derived from the expressions (9) and (10).

$$\frac{G4}{G3}\frac{T2}{T1}\frac{V3}{V4} = \cos^2(\theta + \theta_0) - \sin^2(\theta + \theta_0) \quad (11)$$
$$= \cos 2(\theta + \theta_0)$$

Accordingly, it is possible to calculate the angle of optical rotation "$\theta$" as in the following expression (12) from the expression (11).

$$\theta = \frac{1}{2}\arccos\left(\frac{G4}{G3}\frac{T2}{T1}\frac{V3}{V4}\right) - \theta_0 \quad (12)$$
$$= \frac{1}{2}\arccos\left(C2\frac{V3}{V4}\right) - \theta_0$$

However, it is replaced with "(G4/G3) (T2/T1)=C2".

Similarly to the first embodiment, even in this case, it is effective when determining two parameter values of "C2" and "$\theta_0$" in the expression (12) by performing a measurement using, for example, two or more substances whose angles of optical rotation are known.

2-3. Flow of Processing

Figure 5:
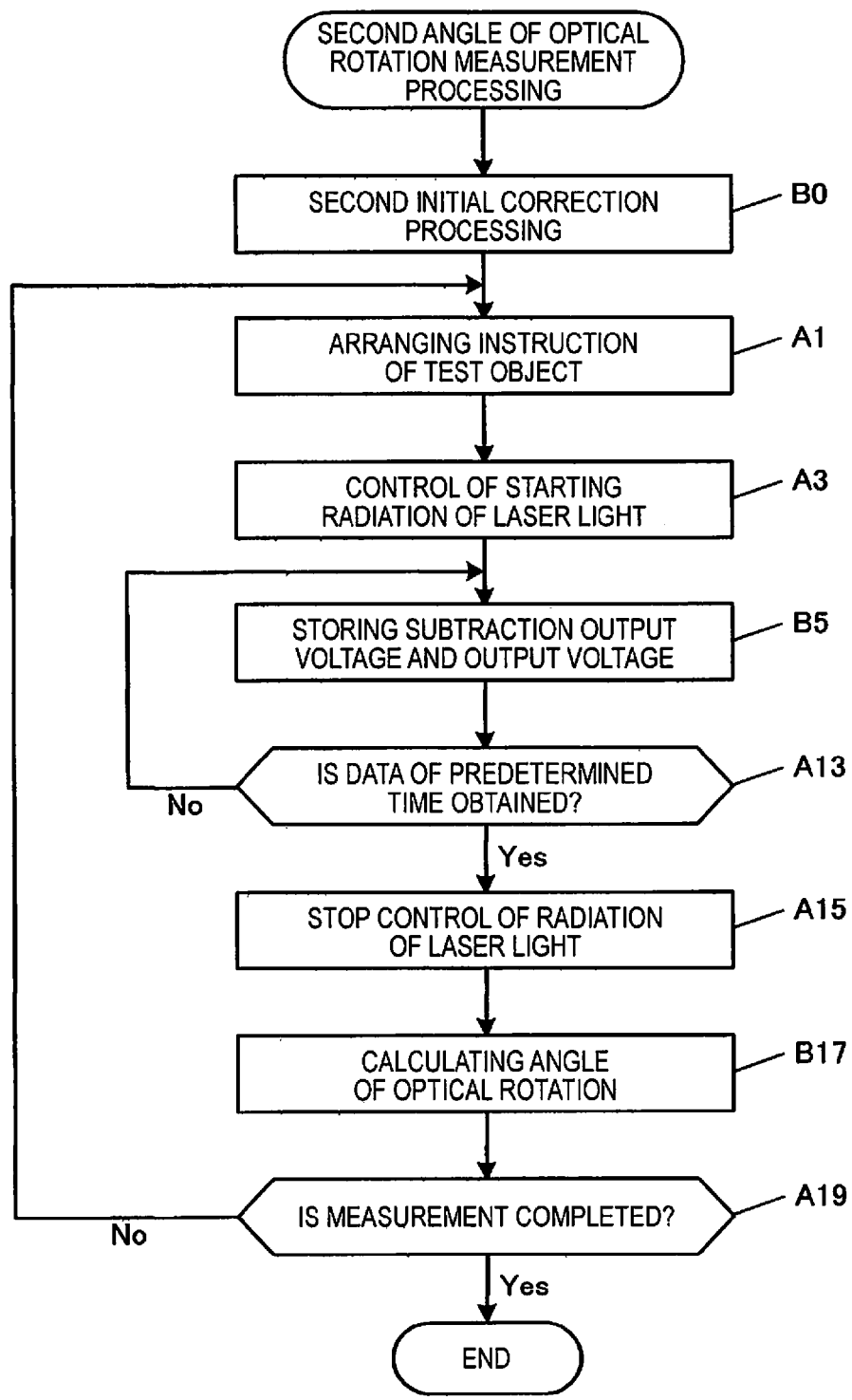
FIG. 5 is a flowchart which illustrates a flow of a second angle of optical rotation measurement processing.

FIG. 5 is a flowchart which illustrates a flow of the second angle of optical rotation measurement processing which is executed by the control unit 100 according to the second angle of optical rotation measurement program 612 which is stored in the storage unit 600. In addition, the same steps as those in the first angle of optical rotation measurement processing are given the same reference numerals, and repeated descriptions will be omitted.

First, the control unit 100 performs second initial correction processing (step B0). Specifically, the two parameter values of "C2" and "$\theta_0$" in the expression (12) are corrected based on the above described method, or the like.

The control unit 100 stores the subtraction output voltage which is output from the second differential amplification unit 70, and the output voltage which is output from the amplification unit 90 in the output voltage data 630 of the storage unit 600 after performing a start control of radiating laser light in step A3 (step B5). In addition, the control unit 100 continuously stores the data of the output voltage until data of the output voltage of a predetermined time is obtained (No in step A13→step B5).

When the output voltage of the predetermined time is obtained (Yes in step A13), the control unit 100 performs a stop control of radiating of the laser light (step A15). In addition, the control unit 100 calculates the angle of optical rotation according to the expression (12) using the parameter value which is corrected in the second initial correction processing, and a mean value of the subtraction output voltage, and a mean value of the output voltage which are stored in the output voltage data 630, and stores the angle of optical rotation in the storage unit 600 as the calculated angle of optical rotation 640 (step B17).

2-4. Effects of Operation

In the second optical measurement device 1B, transmitted light in which the linearly polarized light which is output from the light source 10, and is converted by the polarizing unit 20 passes through the test object A is subject to the non-polarizing separation in a predetermined proportion by the non-polarizing separation unit 25. In addition, light on one side which is subject to the non-polarizing separation is received in the second light receiving unit 80. In addition, light on the other side which is subject to the non-polarizing separation is orthogonally separated by the orthogonal separation unit 30.

In addition, the control unit 100 determines the amount of light of the transmitted light based on the light receiving level in the second light receiving unit 80, and calculates the angle of optical rotation after normalizing a difference between the received light levels in the light receiving unit 40 using the determined amount of light.

In the second optical measurement device 1B, the difference between the received light levels is normalized using the amount of light which is subject to the non-polarizing separation by the non-polarizing separation unit 25, not normalizing the difference in the received light levels using the amount of light of the transmitted light corresponding to the sum of the received light levels which are received in the light receiving unit 40. The amount of light of the transmitted light is determined by adopting a simple configuration in which the transmitted light is subject to the non-polarizing separation by the non-polarizing separation unit 25, and light on one side thereof is received in the second light receiving unit 80. In addition, it is possible to accurately calculate the angle of optical rotation even when a fluctuation in the amount of light of the transmitted light occurs by normalizing the difference between the received light levels in the light receiving unit 40 using the determined amount of light.

3. Modification Example

Embodiments to which the invention is applied are not limited to the above described embodiments, and as a matter of course, the embodiments can be appropriately changed without departing from the scope of the invention. Hereinafter, modification examples will be described.

3-1. Application Example

The optical measurement devices which are described in the above described embodiments (first optical measurement device 1A, and second optical measurement device 1B) can be used by being incorporated in measuring equipment, for example, sugar measuring equipment which measures sugar in fruits, blood sugar level measuring equipment which measures a human blood sugar level.

When the optical measurement device is applied to the sugar measuring equipment, an angle of optical rotation is calculated by radiating linearly polarized light to, for example, fruit juice of fruit as a test object A. In addition, when the optical measurement device is applied to the blood sugar level measuring equipment, the angle of optical rotation is calculated by radiating the linearly polarized light to a portion to be measured, by setting portions having transmitting property such as an earlobe, fingertips, epidermis parts of fingers as portions to be measured. In addition, the sugar of fruit, or the human blood sugar level can be obtained based on the calculated angle of optical rotation.

3-2. Amplification Factor of Differential Amplification Unit

In the above described embodiments, the amplification factor was set to be switched in a case in which the difference between the received light levels is calculated, and in a case in which the sum of the received light levels is calculated by the differential amplification unit 50 of the first optical measurement device 1A, however, a method of variably setting the amplification factor of the differential amplification unit 50 is not limited to this. For example, the amplification factor of the differential amplification unit 50 may also be variably set based on the difference between the received light levels which are calculated in the differential amplification unit 50. The smaller the difference between the received light levels, it is effective to set the amplification factor high.

In addition, when it is possible to measure absorbance of an component which is included in the test object A, it is also possible to variably set the amplification factor of the differential amplification unit 50 based on the magnitude of the absorbance. When the absorbance of the component which is included in the test object A is large, the amount of light in the transmitted light is reduced. For this reason, it is possible to perform a measurement of the transmitted light in a wide dynamic range by setting the amplification factor of the differential amplification unit 50 high, and amplifying the difference between the received light levels with a high amplification factor.

In addition, the amplification factor of the differential amplification unit 50 may be variably set based on the magnitude of the angle of optical rotation. It is possible to measure the angle of optical rotation in a wide dynamic range by setting the amplification factor of the differential amplification unit 50 high, and amplifying the difference between the received light levels with a high amplification factor, when the angle of optical rotation is small.

The above described setting method of the amplification factor can be similarly applied to the second differential amplification unit 70 of the second optical measurement device 1B, as well. That is, it is also preferable to variably set the amplification factor of the second differential amplification unit 70 based on the difference between the received light levels which is calculated in the second differential amplification unit 70. In addition, the amplification factor of the second differential amplification unit 70 may be variably set based on the absorbance of an component which is included in the test object A, or the magnitude of the angle of optical rotation.

3-3. Calculation Method of Angle of Optical Rotation

According to the above described embodiment, the angle of optical rotation was calculated using a mean value of an output voltage of a predetermined time, however, a calculation method of an angle of optical rotation is not limited to this. For example, as a matter of course, the angle of optical rotation may be calculated using an instantaneous value of an output voltage. In addition, it is also possible that angles of optical rotation of a predetermined time, or of a predetermined number are calculated by repeating a step of calculating the angle of optical rotation using the instantaneous value of an output voltage, and the angle of optical rotation is calculated by calculating the average of these angles of optical rotation.

3-4. Optical Element for Polarization

According to the above described embodiment, it has been described that the polarizing unit 20 is configured by including, for example, the Glan Thompson prism, however, it is natural to have a configuration in which other optical element for polarization than that is included. For example, it is also possible to have a configuration in which the Glan Tailor prism which is the same Glan-type optical element for polarization is included.

In addition, according to the above described embodiment, it has been described that the orthogonal separation unit 30 is configured by including, for example, the Wollaston prism, however, it is possible to suitably change the optical element for polarization which configures the orthogonal separation unit 30. For example, it is also possible to have a configuration in which an optical element for polarization having a function of orthogonal separation such as the Glan Laser prism, or a lotion prism is included.

A first aspect is directed to an optical measurement device which includes an orthogonal separation unit which orthogonally separates transmitted light in which linearly polarized light has passed through a test object; at least two light receiving units which receive light which is orthogonally separated in the orthogonal separation unit; and an angle of optical rotation calculation unit which includes a transmitted amount of light determination unit which determines amount of light of the transmitted light, or amount of light of a predetermined proportion of the amount of light, and calculates an angle of optical rotation after normalizing a difference between the received light levels which are received in the light receiving unit using the amount of light which is determined in the transmitted amount of light determination unit.

In addition, as another aspect, the embodiment may be configured as an optical measurement method which includes orthogonally separating transmitted light in which linearly polarized light passes through a test object; receiving the orthogonally separated light; determining amount of light of the transmitted light, or amount of light of the predetermined proportion of the amount of light; and calculating an angle of optical rotation after normalizing a difference between the received light levels using the determined amount of light.

According to the first aspect or the like, the transmitted light in which the linearly polarized light passes through the test object is orthogonally separated, and the orthogonally separated light is received. In addition, the amount of light of the transmitted light, or amount of light of the predetermined proportion of the amount of light is determined, and the angle of optical rotation is calculated after normalizing the difference between the received light levels in the light receiving unit using the determined light. By normalizing the difference between the received light levels, it is possible to correctly calculate the angle of optical rotation, even in a case in which a fluctuation in the amount of light of the transmitted light occurs.

As a second aspect, the optical measurement device according to the first aspect may be configured such that the optical measurement device includes the angle of optical rotation calculation unit which has a differential amplification unit obtaining a difference between the received light levels, and further has an amplification factor setting unit which variably sets an amplification factor of the differential amplification unit.

According to the second aspect, the difference between the received light levels is obtained by the differential amplification unit. The amplification factor of the differential amplification unit is variably set by the amplification factor setting unit. For example, by variably setting the amplification factor based on absorbance of the test object, and the magnitude of the angle of optical rotation, it is possible to calculate the angle of optical rotation in a wide dynamic range.

As a third aspect, the optical measurement device according to the first or second aspect may be configured such that the transmitted amount of light determination unit determines the amount of light using the sum of the received light levels which are received in the light receiving unit.

According to the third aspect, it is possible to simply determine the amount of light of the transmitted light using the sum of the received light levels which are received in the light receiving unit.

As a fourth aspect, the optical measurement device according to the first or second aspect may be configured such that the optical measurement device further includes a non-polarizing division unit which divides the transmitted light using the predetermined proportion in a non-polarizing manner, and a second light receiving unit which receives light on one side which is divided in the non-polarizing manner are further included, in which the orthogonal separation unit orthogonally separates light on the other side which is divided in the non-polarizing manner, and the transmitted amount of light determination unit determines amount of light of the transmitted light of the predetermined rate based on the light receiving level of the second light receiving unit.

According to the fourth aspect, the transmitted light is divided at the predetermined rate in the non-polarizing manner by the non-polarizing division unit. In addition, the light on one side which is divided in the non-polarizing manner is received in the second light receiving unit. In contrast to this, the light on the other side which is divided in the non-polarizing manner is orthogonally divided in the orthogonal separation unit. In addition, the amount of light of the transmitted light of the predetermined rate is determined based on the light receiving level of the second light receiving unit. It is possible to determine the amount of light of the transmitted light of the predetermined rate by adopting a simple configuration in which the transmitted light is divided in the non-polarizing manner by the non-polarizing division unit, and the light on one side is received in the second light receiving unit.

The entire disclosure of Japanese Patent Application No. 2012-016737, filed on Jan. 30, 2012, is expressly incorporated by reference.

What is claimed is:

1. An optical measurement device comprising:
    an orthogonal separation unit configured to orthogonally separate transmitted light in which linearly polarized light has passed through a test object;
    at least two light receiving units configured to receive light which is orthogonally separated in the orthogonal separation unit; and
    an optical rotation angle calculation unit including
        a transmitted light amount determination unit configured to determine amount of light of the transmitted light,
        an amplification factor setting unit configured to set a first amplification factor to the amount of light of the transmitted light and set a second amplification factor to a difference between received light levels which are received in the light receiving units, the first amplification factor and the second amplification factor being different from each other,
        an amplification unit configured to amplify the amount of light of the transmitted light with the first amplification factor and the difference between the received light levels with the second amplification factor, and
        a controller configured to calculate an angle of optical rotation after normalizing the difference between the received light levels using the amount of light of the transmitted light.

2. The optical measurement device according to claim 1, wherein
    the optical rotation angle calculation unit has a subtractor obtaining the difference between the received light levels.

3. The optical measurement device according to claim 1, wherein
    the optical rotation angle calculation unit has an adder obtaining a sum of the received light levels which are received in the light receiving unit, and
    the transmitted light amount determination unit determines the amount of light using the sum of the received light levels.

* * * * *